(12) United States Patent
Marchal et al.

(10) Patent No.: US 6,971,262 B1
(45) Date of Patent: Dec. 6, 2005

(54) SYSTEM AND METHOD FOR RHEOLOGICAL CHARACTERIZATION OF GRANULAR MATERIALS

(75) Inventors: Philippe Marchal, Ludres (FR); Lionel Choplin, Strassen (LU); Nadia Smirani, Nancy (FR)

(73) Assignee: Waters Investment Limited, New Castle, DE (US)

( * ) Notice: Subject to any disclaimer, the term of this patent is extended or adjusted under 35 U.S.C. 154(b) by 0 days.

(21) Appl. No.: 10/875,385

(22) Filed: Jun. 25, 2004

(51) Int. Cl.[7] ............................................. G01N 11/00
(52) U.S. Cl. ...................... 73/54.01; 73/54.24; 73/570; 73/514.15
(58) Field of Search .......................... 73/54.01, 54.24, 73/54.02, 488, 514.15, 514.29

(56) References Cited

U.S. PATENT DOCUMENTS

| | | | |
|---|---|---|---|
| 4,016,766 A * | 4/1977 | Morris | ......................... 73/488 |
| 5,321,974 A * | 6/1994 | Hemmings et al. | ........ 73/54.31 |
| 6,113,976 A * | 9/2000 | Chiou et al. | ................. 426/661 |
| 6,227,039 B1 * | 5/2001 | Te'eni | ........................ 73/54.03 |
| 2003/0067225 A1 * | 4/2003 | Yokota et al. | ................. 310/11 |
| 2003/0200901 A1 * | 10/2003 | Yamamuro et al. | ......... 106/724 |

OTHER PUBLICATIONS

Marchal et al.; "Rheology of Free-Flowing Granular Materials"; Progress and Trends in Rheology V, (I. Emri, Ed.) Steinkopff Darmstast, pp. 206-207 (1998).

Ait-Kadi et al.; "Quantitative Analysis of Mixer-Type Rheometers Using Couette Analogy"; Chemical Engineering Department and Cerism, Laval University, Quebec, Canada and Ensic/Gemico, Nancy, France.

Zik et al.; "Mobility of a Sphere in Vibrated Granular Media"; pp. 315-319; (1992) Europhysics Letters.

Barois-Cazenave et al.; "Experimental Study of Powder Rheological Behaviour" (article); 1999; pp. 58-64; Elsevier Science S.A.; France.

* cited by examiner

Primary Examiner—Hezron Williams
Assistant Examiner—Rodney Frank
(74) Attorney, Agent, or Firm—Pillsbury Wintrhop Shaw Pittman LLP

(57) ABSTRACT

A system for characterizing rheological properties of granular material. A cylindrical measurement cup containing granular material is subject to a uniform vibration induced by a vibration exciter at a user-determined frequency. At the same time, a rotation or an oscillation of a rotating vane tool is performed within the powder and a response measured. Baffles are affixed to the inner wall of the measurement cup to prevent slippage of the granular material during measurement. An energy imparted to the system from the vibration exciter can be measured by an accelerometer coupled to the measurement cup. When sufficient vibrational energy is supplied to the system, a powder contained therein achieves a particle "temperature" sufficient such that the powder behaves as an ergodic system. The visco-elastic properties of the ergodic powder can be reproducibly measured in accordance with known methodology used in molecular fluids, where the powder "temperature" can be varied by changing the vibration frequency or amplitude.

22 Claims, 8 Drawing Sheets

SYSTEM AND METHOD FOR RHEOLOGICAL CHARACTERIZATION OF GRANULAR MATERIALS

BACKGROUND

1. Field of the Invention

The present invention relates generally to scientific instrumentation and in particular to applying rheology to the characterization of granular materials.

2. Background of the Invention

Knowledge of rheological properties of granular materials (also termed "powders") such as foods, cosmetics, pharmaceuticals, paints, coatings, cements, and other materials is of paramount interest in the preparation and use of such materials. Physical characteristics of granular materials such as particle size, shape, size distribution, and hardness all affect the powder flow properties. Because of the inherent metastability of powders in relation to their flow properties, conventional rheometric analysis does not provide a reliable means for measuring powder behavior as described below.

Properties of powders in their normal state are such that the flow behavior observed is unpredictable. These properties often depend on the details of grain arrangements within the powder, which can vary in an unpredictable manner. Therefore, the overall flow behavior is unstable, resulting in great variability in conventional rheological measurements used to try to assess the powder properties. In a prior attempt to address this problem, in "Rheology of Free-Flowing Granular Materials," Progress and Trends in Rheology V, (I. Erni, Ed.) Steinkopff Darmstadt, 206–207 (1998), co-authored by two of the present inventors and incorporated by reference herein in its entirety, Marchal et al. reported use of an elastic vibrating membrane to induce more uniform behavior in a powder and thereby facilitate meaningful rheological measurements. By inducing vibrations within the powder, the authors suggested that a random motion equivalent to Brownian motion among the grains of a powder could be induced. Once the macro Brownian state is induced, the powder could then exhibit a more reproducible rheological behavior that can be probed using conventional rheological methods.

In the above reference, Marchal et al. further suggested that changes in the vibration frequency of a powder act to modify the rheological powder behavior in a manner analogous to increasing the temperature of a viscous fluid. FIG. 1 illustrates a prior art measurement system (based on an adapted Rheometric Scientific SR 200 rheometer) used by the authors for rheological characterisation of vibrated powders. System 100 includes a measurement cell 102 and a rotating vane tool 104 placed within the measurement cell to perform rheological measurements on powder 106 based on the known Couette geometry often used for measurement of viscous materials.

FIG. 2 illustrates the basic principles of Couette geometry as applied to fluid rheological measurements. A fluid (not shown) is sheared between concentric cylinders 200, 202, of height and radius R1, R2, respectively. This shearing is accomplished by imposing a relative rotational motion between the cylinders, for example, by imposing a rotation on inner cylinder 202 while holding outer cylinder 200 stationary. Viscous material within the outer cylinder will tend to resist motion against viscous material moving in the inner cylinder.

Relative motion of viscous material within the inner cylinder may typically be accomplished by applying a rotational (or oscillational) motion to a vane tool such as tool 104 depicted in FIG. 1. While rotating, vane tool 100 forces material between vanes to move in concert with the inner cylinder defined by the vanes. A rotational force (torque $\Gamma$) is applied and a velocity response measured, from which viscosity data can be extracted. Ideally, to obtain correct measurements, the viscous fluid velocity at the outer diameter wall is zero.

FIG. 1 further illustrates a flexible vibrating membrane 108 coupled to a vibration source 110. Vibrating membrane 108 induces vibrations within a powder placed in the cell 102. By imparting vibration into a powder and measuring the powder properties, improved rheological measurements for powders may be obtained. Data taken using a prior art system 100 as depicted in FIG. 1 is reported in the above reference and shows qualitatively that vibration frequency does influence the measured viscosity properties of a powder.

The data obtained using the apparatus of FIG. 1, however, were not sufficiently reproducible. In particular, prior art system 100 does not induce uniform vibrations within a powder contained in cell 102. Vibration exciter 108, composed of an electromagnet with an iron core, introduces vibrations through pulses located at the center of the cell, which does not impart a uniform vibration within the powder in cell 102. In addition, heating of the electromagnet causes extensive heating of measurement cell 102, which may alter measurements and reduce the length of a measurement. Accordingly, information based on an average powder "temperature" is difficult to reproducibly acquire. Furthermore, for meaningful viscosity data to be extracted using a Couette geometry, it is assumed that the "fluid" velocity at the outer cylinder wall is zero. In cell 102, it is not clear that powders contained therein will exhibit such behavior. Therefore, true viscosity data for a powder contained in cell 102 could not be reproducibly obtained using system 100.

In light of the foregoing, it will be appreciated that a need exists for improved techniques to assess the rheological behavior of powder materials.

BRIEF SUMMARY

In an embodiment of the present invention, a system for improved characterization of the rheological properties of granular solid matter includes a measuring cell that includes a cylindrical cup for housing the granular material to be measured. The measurement cell and granular matter contained therein are put into vibration using, for example, a vibration exciter coupled to the cylindrical cup, which is preferably rigid. The vibration exciter may contain a magnet, an electromagnet, or other device capable of inducing vibrations within the cup. The vibration exciter is coupled to the measuring cell cup in a manner that imparts a uniform vibration within the measuring cell and a powder contained in the measurement cell. A rotating vane tool whose rotation axis is concentric with the cylinder axis of the measuring cell is inserted within the measuring cell to impart a shear motion within the granular matter. Preferably, a series of baffles are affixed to the inner side of the vertical cylinder wall of the measuring cell cup to prevent slippage of the powder and improve the accuracy of rheological measurements. An accelerometer coupled to the measuring cell is configured to measure the vibration amplitude and acceleration of the granular matter. Accordingly, the vibration frequency dependence of the rheological properties of granular material can be reproducibly measured in real time.

In another embodiment of the present invention, a method for determining the rheological properties of a powder comprises placing the powder in a cylindrical cup. Preferably, the cylindrical cup is constructed of a rigid transparent material. After placing the powder in a cup, the powder is excited by inducing a uniform vibration within the powder. Preferably, the uniform powder vibration is induced by causing the cup to vibrate uniformly. In one embodiment, a rigid cup is affixed to a vibration exciter thereby setting the cup into uniform vibration when the vibration exciter is operating. By introducing a shear motion within the powder while it is subject to uniform vibration, and detecting a velocity induced by the shear motion, the rheological properties of the powder are determined.

In a further embodiment of the present invention, a method for measuring the rheological properties of an ergodic powder includes placing the powder to be measured in a cup. A shear motion is induced in the powder, preferably by causing an inner cylinder of powder within the cup to oscillate within an outer cylinder of powder within the cup. A uniform vibration is induced within the powder at a frequency and amplitude sufficient to impart a macro-kinetic energy of the powder, where rapid rearrangement of powder grains occurs. The rapid rearrangement of grains induces an average property to the powder that can be characterized by a powder macro-temperature that is proportional to the amplitude and/or frequency of the vibrations within the powder.

DETAILED DESCRIPTION OF THE PREFERRED EMBODIMENTS

Figure 3:
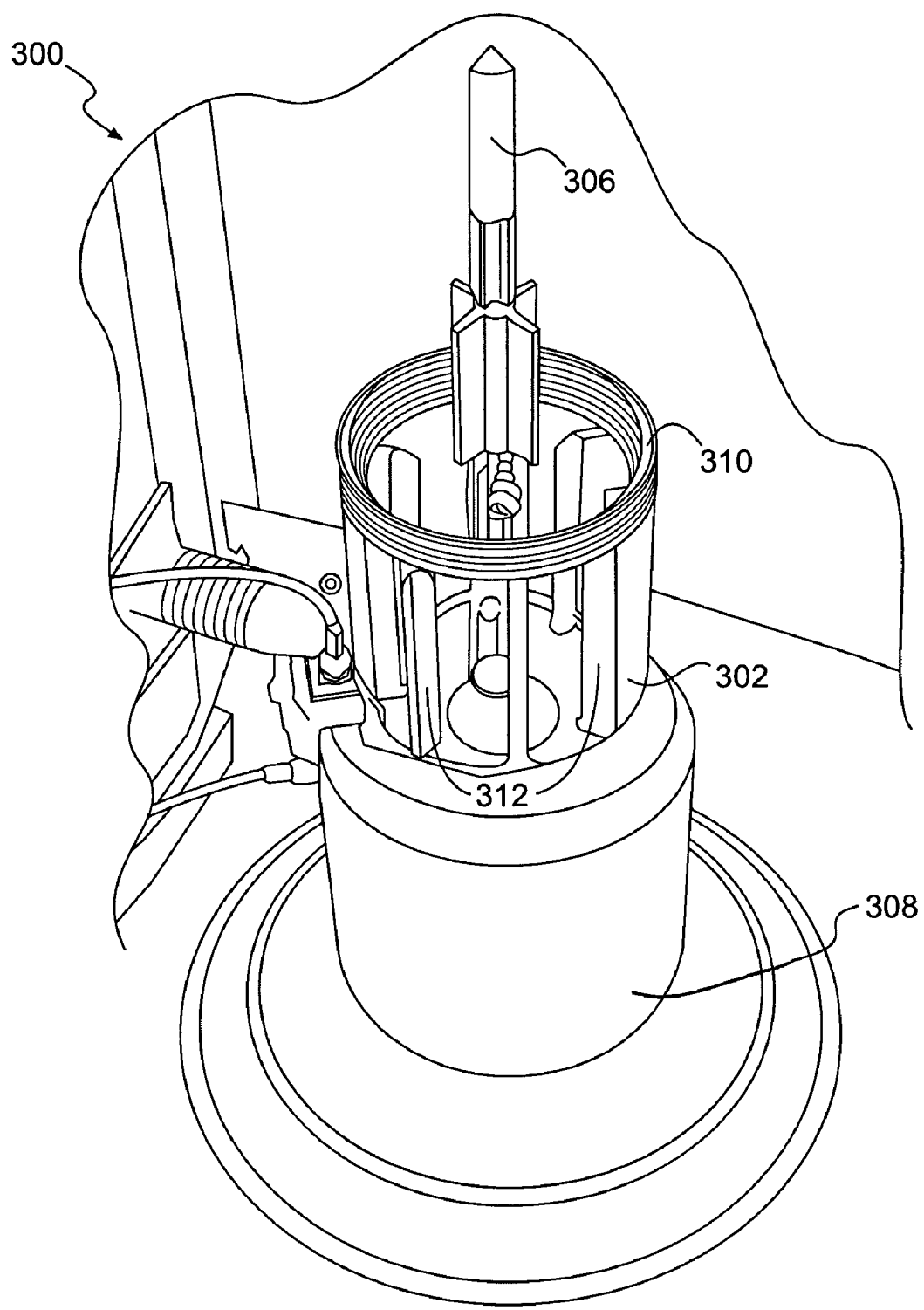
FIG. 3 depicts features of a rheological measurement cell, according to an embodiment of the present invention.

FIG. 3 depicts portions of a rheology measurement system 300 in accordance with an exemplary embodiment of the present invention. The system comprises a cylindrical measurement cell 302 that is used to house granular material to be measured.

The granular material to be measured (not shown) may contain grains (or "particles") of a range of average size; in a preferred embodiment, the average grain size of material to be measured is in the range of about 10 micrometers to about 1 millimeter. The "average" particle size may, for example, refer to the mean size or the mode size according to the known statistical meaning of the words "mean" and "mode." Moreover, in general, individual powder particles need not be equi-axed in shape, but may comprise platelet-like structures, elongated structures, a mix of structures, and other structures.

Measurements are performed with the aid of a rotating vane tool 306 introduced in cell 302 along the cylinder axis. The rotating vane tool operates to introduce a shear force within an assemblage of grains within the measurement cell. A torque is applied to rotating vane tool 306 and a response velocity is measured, from which the rheological properties of the granular material can be determined.

System 300 further includes a vibration exciter 308 coupled to measurement cell 302, for example, through the bottom of the cylinder that forms the cup 310 for measurement cell 302. System 300 is designed such that vibration exciter 308 imparts a uniform vibration pattern within cup 310 and thereby a uniform vibration pattern within powder contained therein. For example, cup 310 may be rigid such that vibrations received from exciter 308 propagate uniformly within cup 310. Preferably cup 310 is firmly affixed to exciter 308 during operation of system 300. Preferably, cup 310 comprises Plexiglas, PVC, or another rigid transparent material. When attached, for example, by a screw to cup 310, exciter 308 may generate sufficient agitation within the powder to establish rheological behavior within the powder similar to polymer systems, as explained further below.

Figure 4A:
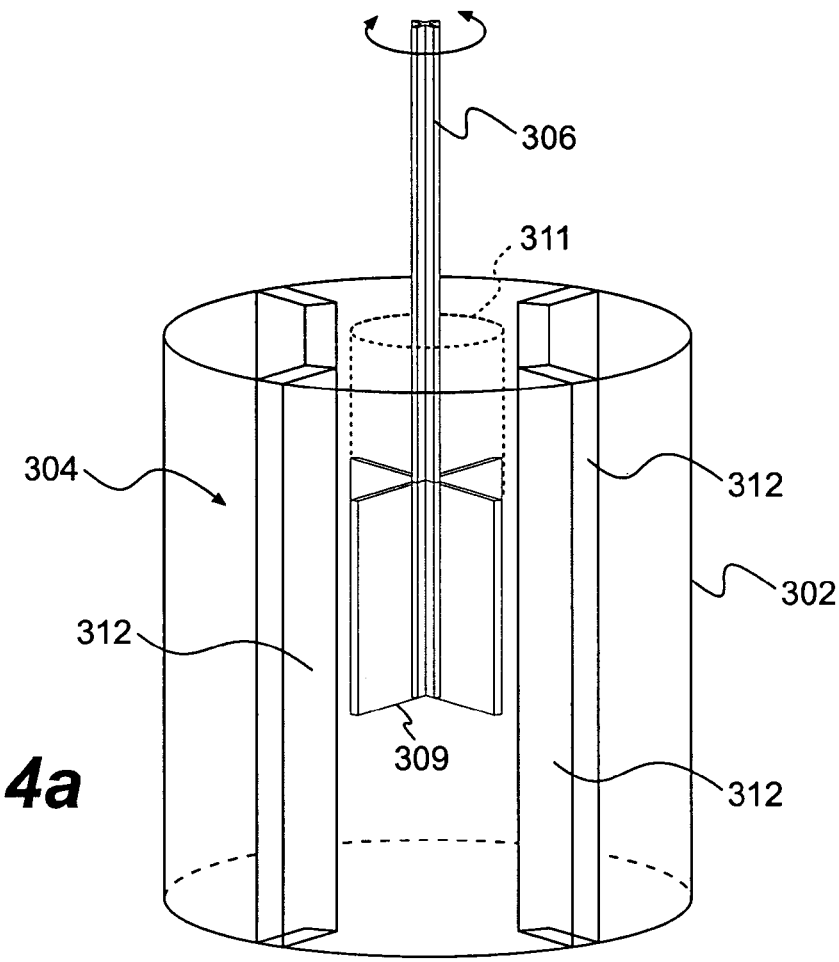
FIGS. 4a and 4b are schematic diagrams that show details of an exemplary rheological measurement cell, according to an embodiment of the present invention.
Figure 4B:
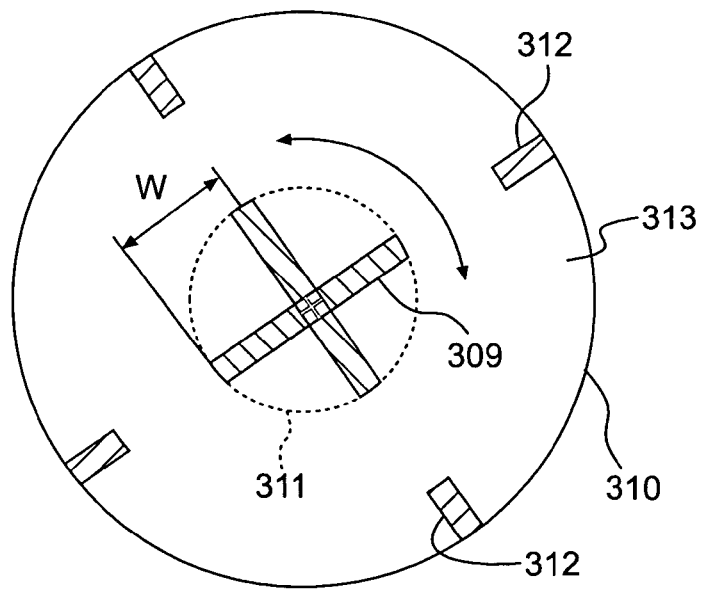

FIGS. 4a and 4b illustrate details of measurement cell 302 according to an exemplary embodiment of the present invention. The arrangement of measurement cell 302 and rotating vane tool 306 placed therein is in accordance with the known Couette geometry often employed to measure rheological properties of fluids as discussed above. As illustrated in FIG. 4a, a rotational or oscillatory motion is imparted to vane tool 306 along its cylinder axis, which is coincident with the axis of cell 302. The rotation (or oscillation) of vanes 309 within a medium of powder 304 that fills measurement cell 302 acts to impose a rotational motion on a cylinder of powder 311 defined by vanes 309, and whose radius is defined by the vane width W, as shown further in FIG. 4b. This motion induces a shear force between the inner cylinder of powder 311 and an outer cylinder of powder 313 lying outside cylinder 311.

Figure 2:
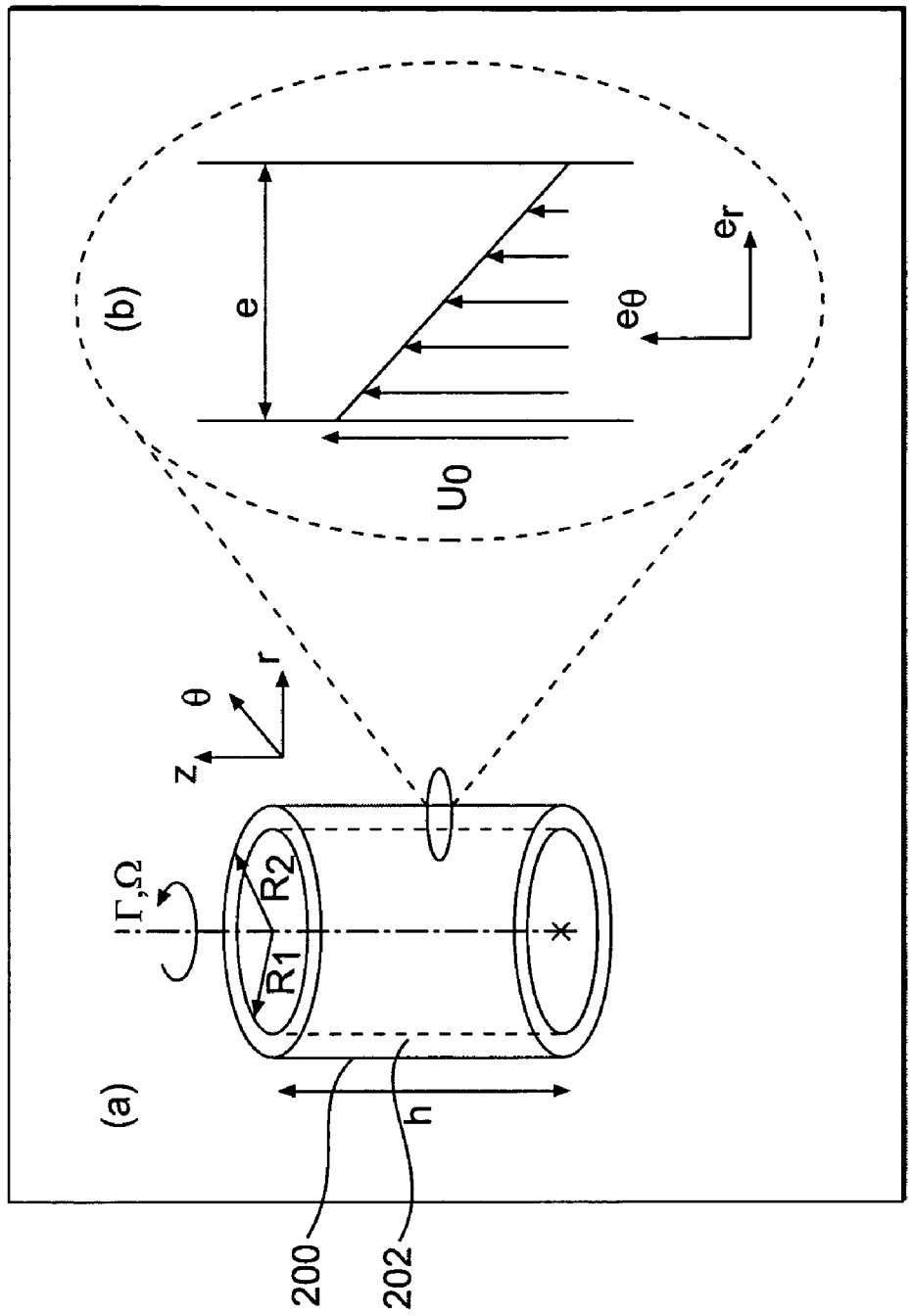
FIG. 2 is a schematic diagram that illustrates details of Couette geometry, which is used to extract rheological information of powders contained in a measurement cell.

Embodiments of the present invention provide an improved ability to simulate the Couette measuring geometry for powder viscosity measurement described above. Preferably, powder placed within measurement cell 302 fills the cell sufficiently to completely immerse vanes 309 within the powder. In order for the ideal Couette measurement conditions to be approximated, the powder velocity at the inner wall of cell 302 must be zero. Known methods for preventing motion of particles at the cell wall include gluing a layer of particles to be measured at the wall. However, such a method is tedious, and requires removal and cleaning each time a new sample is measured. A preferred embodiment of the present invention affixes baffles 312 to the inner wall of cell 302. Baffles 312 are provided to prevent slippage of powder near the wall of measurement cell 302, as illustrated in FIGS. 4a and 4b. The baffles may run substantially the height of the cylinder forming the cup. Although not depicted for clarity, in a preferred embodiment, eight baffles 312 are placed within cell 302 and affixed to the inner wall of cup 310. By preventing powder slippage at the walls, the powder velocity at the cell wall is maintained at zero, and the Couette condition depicted in FIG. 2 is maintained, so that, for example, viscosity data can properly be determined from velocity measurements.

Furthermore, as described below, embodiments of the present invention impart vibrational motion throughout the powder placed within measurement cell 302, to impart energy sufficient to cause the powder to behave in a manner analogous to a viscous fluid. Accordingly, rheological properties of granular solids can be determined and systematically studied similarly to "classic" fluids, such as polymer systems.

Figure 1:
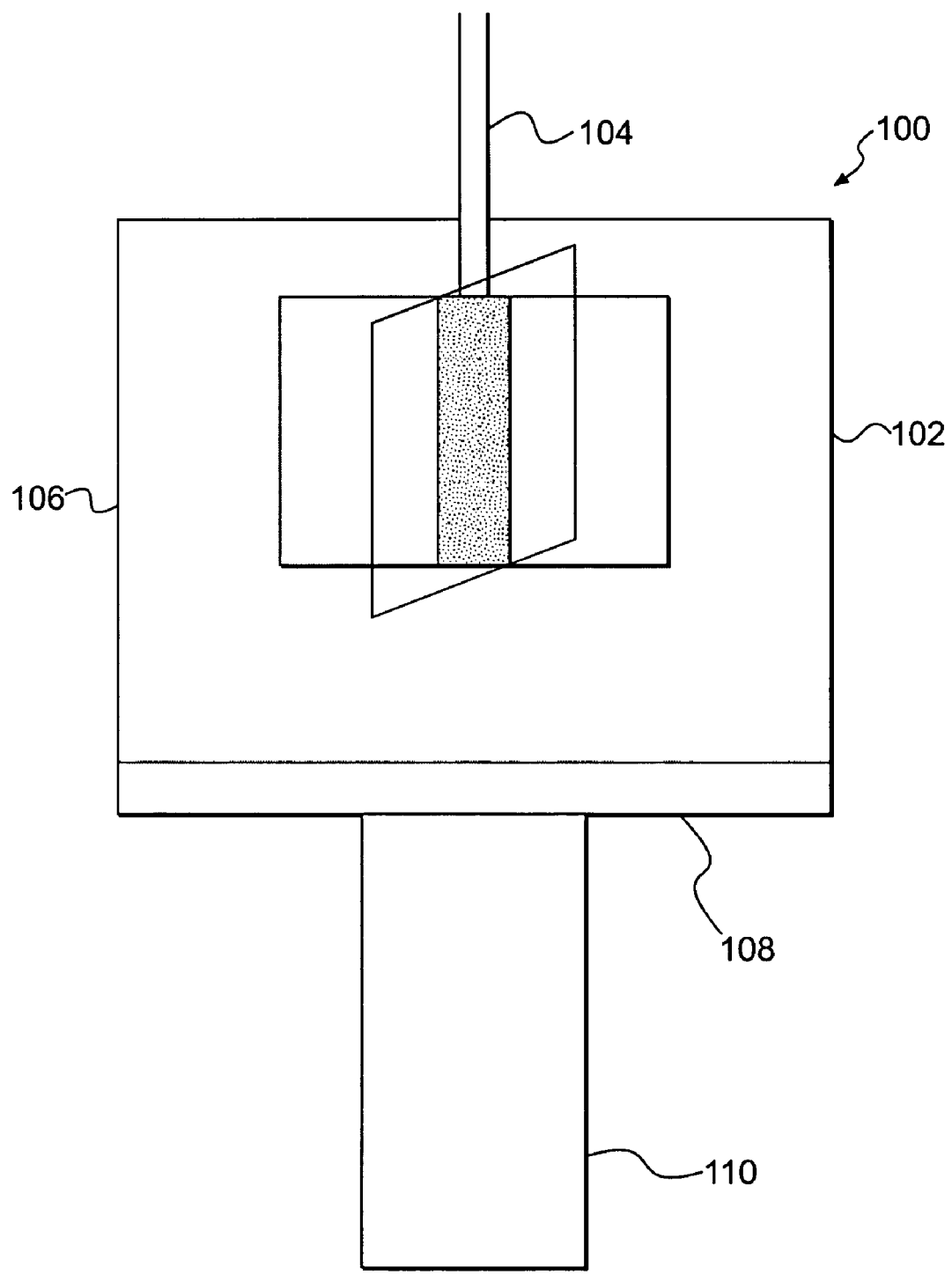
FIG. 1 is a schematic diagram that depicts a rheological measurement system according to the prior art.
Figure 5:
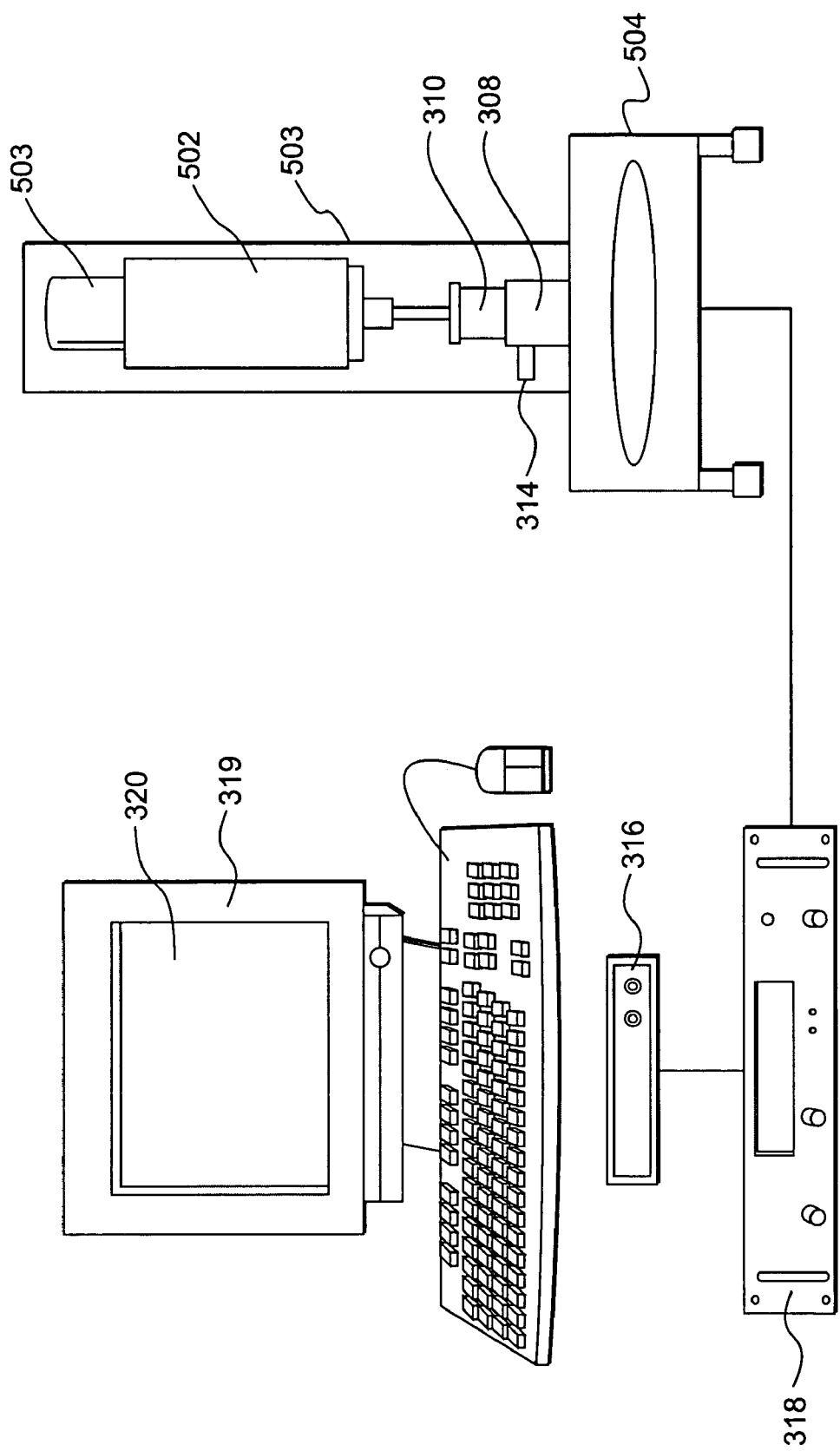
FIG. 5 is a schematic diagram that shows an exemplary rheological measurement system, according to an embodiment of the present invention.

Referring to FIG. 5, in a preferred embodiment of the present invention, vibration exciter 308 imparts vibrations (or "mechanical vibrations") uniformly within the measurement cell cup 310, which in turn imparts a uniform mechanical vibration within powder material contained therein (not shown). During viscosity measurement of the vibrating powder, a drive motor (not shown) within stage 502 affixed to guiding pillar 503, causes rotating vane tool 104 (See FIG. 1) to oscillate within a powder contained in cup 310. Preferably, a user inputs rheological test parameters using test computer 319, which is additionally configured to communicate with a rheometer control computer (not shown) that accepts input from test computer 319 and controls the actions of the rotating vane tool during a measurement. During a measurement, or subsequently, test data can be displayed on a display screen 320 within computer 319.

Function generator 316 can provide sinusoidal, pulse, creneaux, random, harmonic series, Brownian, or custom-designed signals to be output to vibration exciter 308, affixed to rheometer base 504. Such signals, amplified as necessary by amplifier 318, provide controlling signals that determine the motion of exciter 308. Preferably, the frequency range of vibration is about 1 to 1000 Hz. In exemplary embodiments of the present invention, sinusoidal vibrations are generated in a frequency range of about 10 to 100 Hz. In other embodiments employing, for example, pulses, excitation frequency as low as one Hz may be appropriate.

Preferably, an accelerometer 314 is coupled to measurement cell 302 to measure the amplitude and velocity of vibrating powder. Optionally, the signal output by the accelerometer could be sent to a measurement amplifier (not shown). An advantage of the use of an accelerometer over prior art methods is that the acceleration, velocity, and amplitude of a vibrating powder can be determined accurately, for example, when a sinusoidal vibration signal is applied to cup 310. Accordingly, the energy of the vibrating powder can be accurately determined in real time. Alternatively, a linear variable differential transformer can be used for the same measurement purposes as accelerometer 314.

In preferred embodiments of the present invention, the mechanical vibrations generated by exciter 308 can be used to impart an equivalent to Brownian motion in the powder particles contained in cell 302. Classical Brownian motion is typical of motion in molecular systems of finite thermal energy. The "macro-Brownian" motion state for a powder in cell 302 is realized when a critical amount of energy is provided to the powder, as described further below.

Properties of powders in the normal, non-macro-Brownian motion state, are such that they can vary unpredictably according to the details of grain arrangement. Flow behavior is unstable and rheological measurements therefore show great variability. However, when the energy provided by exciter 308 exceeds a threshold, which may be estimated empirically, a powder contained within cell 302 will exhibit a macro-Brownian motion. Once the macro-Brownian motion state is induced, the powder exhibits a reproducible rheological behavior that can be characterized using the Couette geometry described above.

When the mechanical energy imparted by vibration exciter 308 increases, the average free volume $V_f$ (Total volume of the powder "body" minus the volume occupied by the powder grains) increases. Above a critical excess free volume, $V_f^* = V_f - V_{fc}$, where $V_{fc}$ is the critical volume, the powder system behaves as an ergodic system, that is, the system displays a stable macroscopic behavior in which the internal rearrangement of grains is rapid and random, thereby imparting an average macroscopic behavior to the assemblage of grains that constitute the powder. The powder particles could then be envisaged to exhibit macro-Brownian motion.

In the regime of mechanical energy that produces an ergodic powder, changes in the energy input into a powder from exciter 308 act similarly to changes in temperature in a conventional polymer system. Accordingly, the rheological properties of powder systems can be probed as a function of a "powder temperature," for example. Referring again to FIGS. 3 and 4a, during a rheological measurement, a vibration is uniformly imparted into a powder contained in cell 302 by means of vibration exciter 308. At the same time, a rotational or an oscillatory motion may be introduced into rotating vane tool 306, inducing a shear between inner cylinder of powder 311 and outer cylinder of powder 313 within which the inner cylinder of powder oscillates, as depicted in FIG. 4b. A response of the powder to a rotational or oscillatory motion or force may be recorded, from which, for example, the viscosity or the mechanical impedance of an ergodic powder subject to a given energy input from vibration exciter 308, may be determined.

A macro-kinetic energy level of an ergodic powder can be estimated by use of accelerometer 314. For example, a sinusoidal vibration induced by vibration exciter 308 operating at frequency f, induces within grains moving with velocity within the powder, an average "macro kinetic energy" $\frac{1}{2} mv^2$, which is proportional to $(dA/dt)^2$, where A is the amplitude of the sinusoidal vibration, and t is time. In turn, $(dA/dt)^2$ is proportional to $^2$. Variations in amplitude or frequency can be used to induce different powder macro kinetic energy values or "macro-temperature" to the powder system. Accelerometer 314 can measure properties such as the acceleration or velocity as a function of time (the "vibration kinetics") of the vibrating cup. Thus, to determine the powder grain macro-kinetic energy, accelerometer 314 can, for example, be used to measure (dA/dt).

A hallmark of the regime of mechanical energy in which the powder is ergodic, is that viscosity measurements as a function of test parameters, such as vibration frequency produces smooth and reproducible data. In preferred embodiments of the present invention, a user tailors the input macro-kinetic energy from vibration exciter 308 such that smooth and reproducible rheology data measurements are obtained, thus ensuring that the powder assumes an ergodic state during measurement. Measurement data thus obtained are substantially free from artifacts encountered in static powders discussed above. To further confirm that a powder subject to vibrations from vibration exciter 308 exhibits Brownian-type motion, vane tool 306 is introduced without any axial torque into powder 304, and angular fluctuations of vanes 309 recorded, from which a power spectrum indicative of Brownian motion can be obtained, as taught in P. Marchal and L. Choplin, Recénts Progrès en Génie des Procédés, 15 (77) (2001) 379–384, and incorporated by reference herein in its entirety.

An advantage of the embodiment of the present invention depicted in FIG. 3 is that vibration exciter 308 can impart vibration within cell 302 without causing excessive heating, so that system heating effects do not significantly degrade powder measurement experiments.

In preferred embodiments of the present invention, the particle diameter of powders measured in cup 302 is about 10 to 1000 micrometers. In principle, the macro-Brownian motion induced in a powder material is not dependent on the average particle size of the powder material. However, if the particle size exceeds the vane width defined in FIG. 4, viscosity measurements determined from the Couette geometry will no longer apply. Moreover, in order to accurately compare viscosity measurements of a powder material that can be prepared and measured at a range of discrete particle sizes, it is preferably that the weight of powder samples placed in cup 302 for each particle size is maintained at a constant level.

Figure 6A:
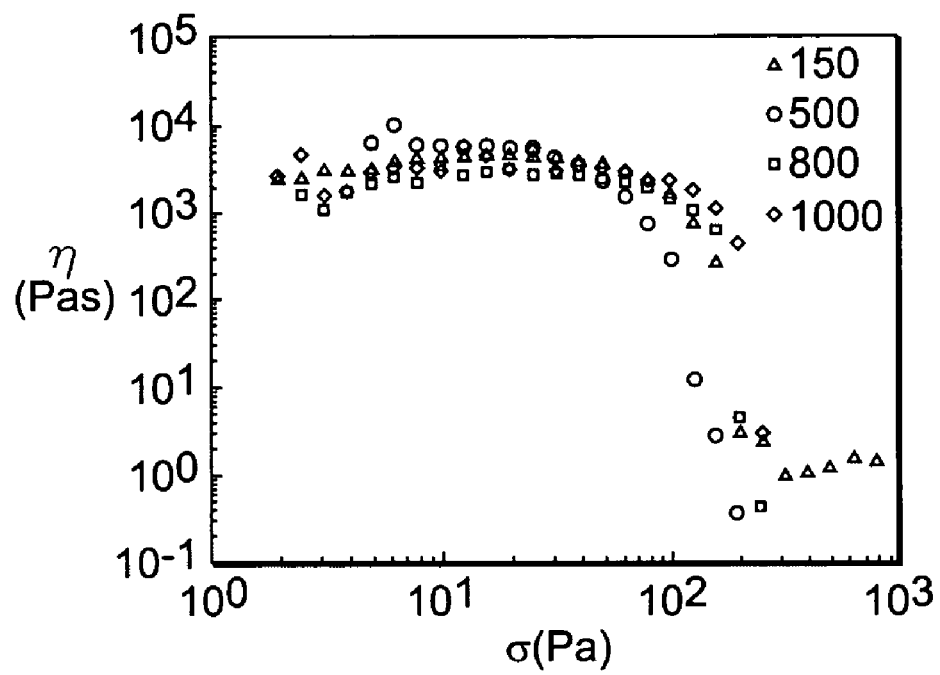
FIG. 6a is a plot of the non-Newtonian viscosity of glass beads of varying diameter as a function of the shear stress, measured in a system arranged according to an exemplary embodiment of the present invention.
Figure 6B:
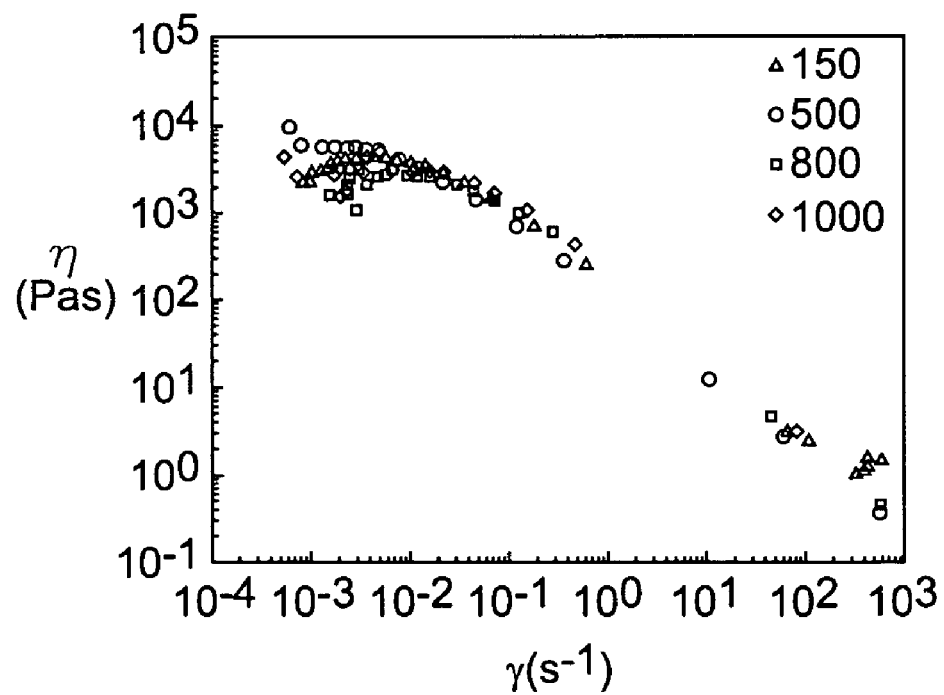
FIG. 6b is a plot of the non-Newtonian viscosity of glass beads of varying diameter as a function of the shear rate, measured in a system arranged according to an exemplary embodiment of the present invention.

FIGS. 6a, 6b, and 7a–7c illustrate examples of rheological data taken in a powder measurement cell constructed according to embodiments of the present invention. FIGS. 6a and 6b depict viscosity as a function of shear stress and shear rate, respectively, in glass bead "powders" for glass bead diameters in the range of about 150 to 1000 micrometers, and for an excitation frequency of 50 Hz. The behavior is reproducible and typical of a viscous liquid, indicating that the 50 Hz excitation used is sufficiently energetic to induce ergodic behavior in the glass bead system.

Figure 7A:
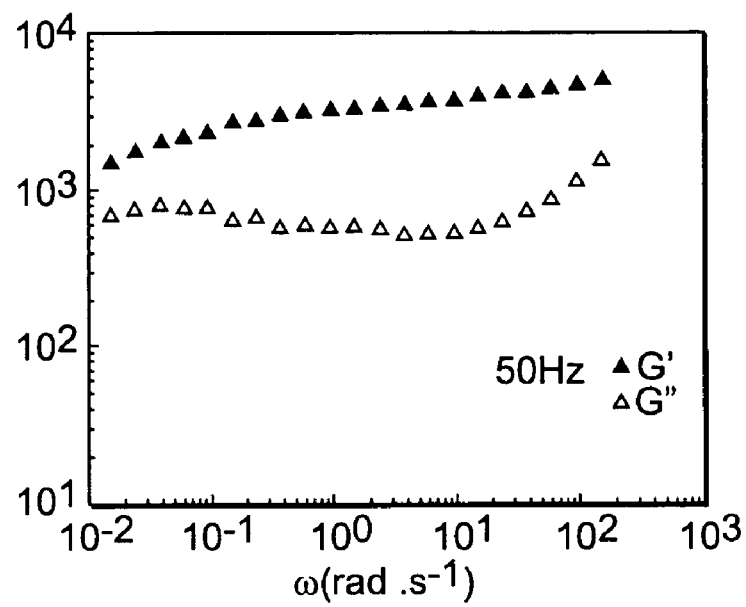
FIG. 7a is a plot of the moduli of semolina powder excited by 50 Hz vibrations as a function of rotating vane tool oscillation pulsation, in a measurement system arranged according to an exemplary embodiment of the present invention.
Figure 7B:
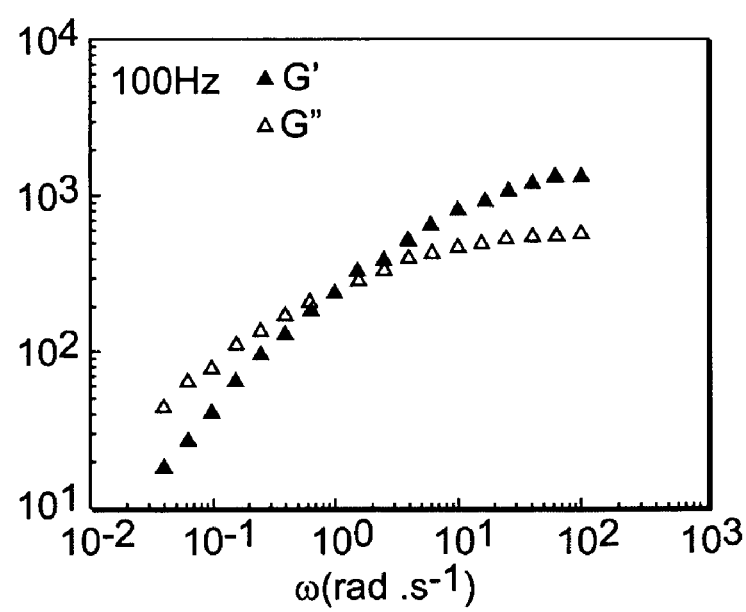
FIG. 7b is a plot of the moduli of semolina powder excited by 100 Hz vibrations as a function of rotating vane tool oscillation pulsation, in a measurement system arranged according to an exemplary embodiment of the present invention.

FIGS. 7a and 7b illustrate elastic and viscous moduli of a semolina powder as a function of oscillation pulsation (pulsation, or ω, is equal to $2\pi(\text{rad.s}^{-1})$, where ν is the oscillation frequency (Hz)) of rotating vane tool 306, for vibration frequencies of 50 and 100 Hz, respectively. As described above, the different vibration frequencies can be thought of as imparting different macro-temperature values to the vibrating semolina powder. At the higher macro-temperature, the moduli are lower and decrease more rapidly as a function of decreasing oscillation pulsation.

Figure 7C:
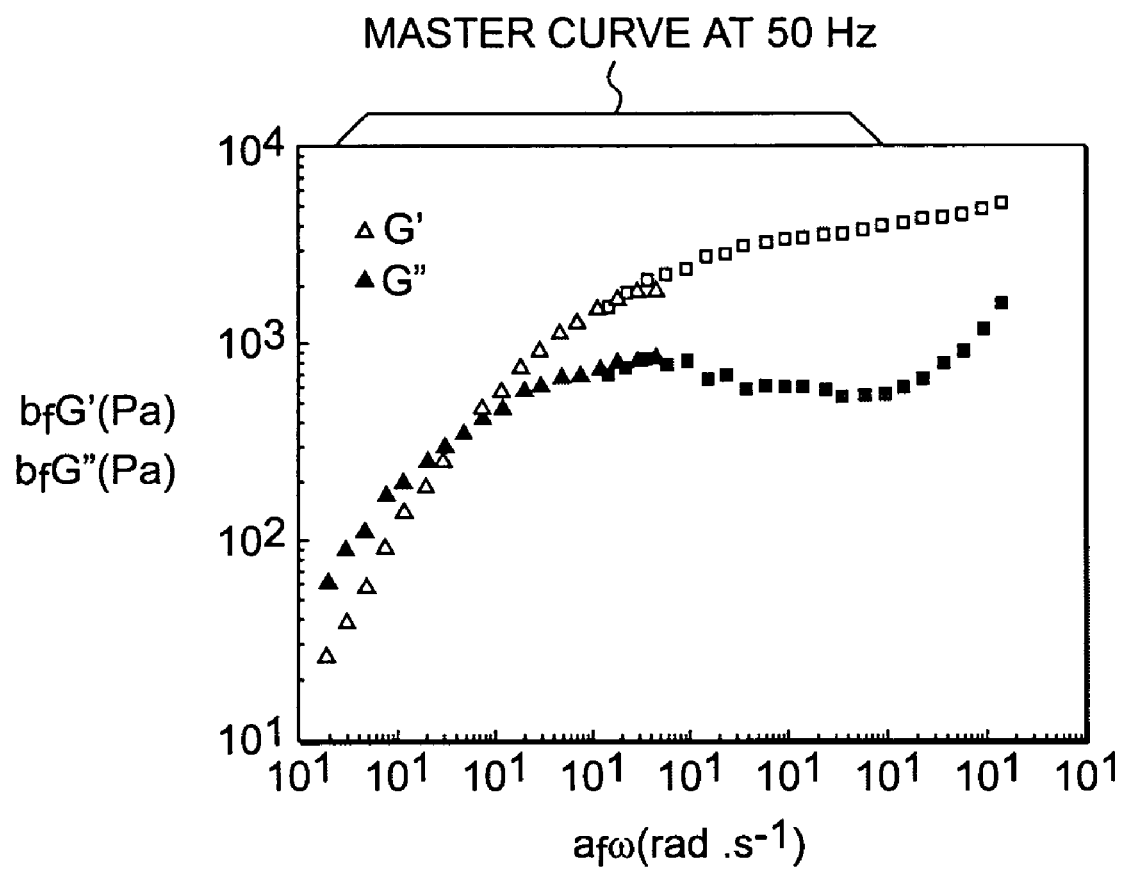
FIG. 7c is a plot of a master curve of the moduli of semolina powder obtained by overlapping the mechanical spectra of FIGS. 7a and 7b, at a 50 Hz reference frequency, as a function of rotating vane tool oscillation pulsation, in a measurement system arranged according to an exemplary embodiment of the present invention, illustrating the occurrence of a "time-granular temperature" superposition principle.

FIG. 7c represents a composite of moduli data depicted in FIGS. 7a and 7b, wherein the 100 Hz data is re-plotted on the 50 Hz coordinates of FIG. 7a. The 100 Hz data is shifted to the left along the oscillation pulsation axis, whereby the curve of 100 Hz and 50 Hz data points overlap. As shown in FIG. 7c, the "master curve" thus generated for 50 Hz excitation of semolina powder represents a composite of the measured and expected oscillation pulsation dependence of the moduli of semolina powder over a wide oscillation pulsation range, corresponding to a powder macro temperature induced by 50 Hz vibration.

The graph and the data depicted in FIG. 7c is typical of "time-temperature" superposition behavior of viscous polymer systems, where a master curve of visco-elastic properties can be obtained for a given temperature by collecting data at different temperatures and realigning the data along, for example, the oscillation pulsation (which is proportional to the oscillatory shear rate) axis according to the polymer temperature. The effect of increased temperature is to shift the modulus versus oscillation pulsation data to the right along the shear rate axis. The ability to demonstrate superposition of the 50 and 100 Hz curves for semolina powder measured in system 300, illustrates that system 300 effectively imparts visco-elastic properties to the powder that are analogous to true molecular fluids.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents. For example, although reference has been made in preferred embodiments to use of a rotating blade viscometer, other geometries, such as mixer geometries are possible. Additionally, other sensors such as position transducers could be used in place of an accelerometer. The advantage of the latter devices are that reliable displacement measurements can be performed on systems subject to pulse vibration, white noise, Brownian noise, and other vibrations.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A system for measuring the rheological properties of a granular material subject to vibration comprising:
   a cylindrical cup adapted to contain the granular material, wherein the cylindrical cup has a cylinder axis;
   a vibration exciter coupled to the cylindrical cup for inducing a uniform vibration within the granular material;
   a rotating vane tool having a rotation axis concentric with the cylinder axis of the cylindrical cup, for imparting a shear motion within the granular material; and
   a strain measurement device coupled to the cylindrical cup for measuring the vibration kinetics of the granular material.

2. The system of claim 1, further comprising a plurality of baffles affixed to the inner wall of the cylindrical cup parallel to the cylinder axis.

3. The system of claim 1, wherein the rotating vane tool comprises a shaft and a plurality of vanes, each vane affixed to the shaft.

4. The system of claim 1, wherein the strain measurement device comprises an accelerometer.

5. The system of claim 1, wherein the strain measurement device comprises a linear variable differential transformer.

6. The system of claim 1, further comprising:
a function generator that generates controlling signals according to the type of vibrations to be generated by the vibration exciter in the cylindrical cup;
a power amplifier in communication with the vibration exciter, wherein the power amplifier amplifies the controlling signals from the function generator; and
a measuring amplifier coupled to the strain measurement device.

7. The system of claim 1, wherein the frequency of vibrations induced by the vibration exciter is between about 1 and 1000 Hz.

8. The system of claim 1, wherein the vibration exciter generates sinusoidal vibrations.

9. A method for determining the rheological properties of a powder comprising:
placing the powder in a cylindrical cup;
inducing a uniform vibration within the powder;
introducing a shear motion within the powder independent of the vibration; and
detecting a velocity induced by the shear motion.

10. The method of claim 9, wherein inducing a uniform vibration within the powder comprises introducing a vibration uniformly within the cylindrical cup.

11. The method of claim 9, wherein the uniform vibration is of sufficient energy to induce the powder to behave as an ergodic system.

12. The method of claim 9, wherein the shear motion is induced by a rotating vane tool oriented along the axis of the cylindrical cup.

13. The method of claim 12, wherein the rotating vane tool is configured to oscillate at a rate between about one hundredth and one hundred radians per second.

14. The method of claim 9, wherein the uniform vibration is a sinusoidal vibration.

15. The method of claim 14, further comprising measuring the vibration energy of the powder, wherein an accelerometer is coupled to the cylindrical cup and is configured to measure the amplitude, velocity, and acceleration of vibrations within the powder.

16. The method of claim 9, wherein the vibration frequency is between one and one thousand Hz.

17. A method for measuring the rheological properties of an ergodic powder comprising:
placing the powder in a cup;
inducing a shear motion within the powder; and
introducing a uniform vibration within the powder at a first frequency and a first amplitude, wherein a macrokinetic energy of the powder vibrating at the first frequency and first amplitude is sufficient to induce a rapid rearrangement of powder grains that causes the powder to exhibit rheological behavior similar to polymer systems.

18. The method of claim 17, wherein the cup is coupled to a vibration exciter that introduces a uniform vibration within the cup.

19. The method of claim 18, wherein the cup is a rigid cup.

20. The method of claim 17, wherein a powder macrotemperature is varied by varying one of the first frequency and the first amplitude.

21. The method of claim 17, wherein an average particle size of the powder is between about one and one thousand micrometers.

22. The method of claim 17, wherein the shear motion within the powder comprises an oscillation of an inner cylinder of powder within an outer cylinder of powder.

* * * * *